(12) United States Patent
Moreau

(10) Patent No.: US 8,246,721 B2
(45) Date of Patent: Aug. 21, 2012

(54) METHOD FOR REMOVING N₂O FROM A GASEOUS FLOW

(75) Inventor: Serge Moreau, Velizy Villacoublay (FR)

(73) Assignee: L'Air Liquide Societe Anonyme pour l'Etude et l'Exploitation des Procedes Georges Claude, Paris (FR)

( * ) Notice: Subject to any disclaimer, the term of this patent is extended or adjusted under 35 U.S.C. 154(b) by 391 days.

(21) Appl. No.: 12/530,715

(22) PCT Filed: Mar. 13, 2008

(86) PCT No.: PCT/FR2008/050424
§ 371 (c)(1),
(2), (4) Date: Sep. 10, 2009

(87) PCT Pub. No.: WO2008/135675
PCT Pub. Date: Nov. 13, 2008

(65) Prior Publication Data
US 2010/0089237 A1    Apr. 15, 2010

(30) Foreign Application Priority Data
Mar. 16, 2007 (FR) ..................... 07 53889

(51) Int. Cl.
*B01D 53/04* (2006.01)
*B01D 53/56* (2006.01)
(52) U.S. Cl. ............. 95/129; 95/139; 128/205.27
(58) Field of Classification Search .......... 95/117, 95/129, 139, 148, 902; 96/132; 128/205.12, 128/205.27, 205.28
See application file for complete search history.

(56) References Cited

U.S. PATENT DOCUMENTS

| 3,592,191 | A | * | 7/1971 | Jackson | 128/203.28 |
| 3,941,573 | A | * | 3/1976 | Chapel | 96/135 |
| 4,259,303 | A | | 3/1981 | Nakaji et al. | |
| 4,355,637 | A | | 10/1982 | Dyer | |
| 5,515,845 | A | * | 5/1996 | Filipovic et al. | 128/205.12 |
| 6,106,593 | A | * | 8/2000 | Golden et al. | 95/120 |
| 6,273,939 | B1 | * | 8/2001 | Millet et al. | 95/106 |
| 6,425,937 | B1 | | 7/2002 | Kraus et al. | |
| 6,682,710 | B1 | | 1/2004 | Hamon et al. | |

(Continued)

FOREIGN PATENT DOCUMENTS

EP    0698411    2/1996

(Continued)

OTHER PUBLICATIONS

Search Report for PCT/FR2008/050424, Oct. 2008.

(Continued)

*Primary Examiner* — Frank Lawrence, Jr.
(74) *Attorney, Agent, or Firm* — Allen E. White

(57) ABSTRACT

The invention relates to a method for purifying a supply gaseous flow containing at least 5 vol. % of N₂O and oxygen, in which: (a) the gaseous flow is contacted with a main adsorbent (3) including at least one zeolite exchanged at more than 50% by one or more metal cations and having an N₂O adsorption capacity, as measured under 1 bar and at 200° C., of more than 80 Ncm/g in order to adsorb at least a portion of the N₂O from said flow and to produce a purified gaseous flow; and (b) recovering a purified gaseous flow having an N₂O content lower than the N₂O content of the supply gaseous flow contacted with the main adsorbent during step (a).

17 Claims, 1 Drawing Sheet

U.S. PATENT DOCUMENTS

| | | | |
|---|---|---|---|
| 6,824,588 B2 * | 11/2004 | Nakamura et al. | 95/117 |
| 7,527,670 B2 * | 5/2009 | Ackley et al. | 95/96 |
| 2005/0098495 A1 * | 5/2005 | Hughes | 210/502.1 |
| 2006/0008401 A1 | 1/2006 | Hotta et al. | |

FOREIGN PATENT DOCUMENTS

| | | |
|---|---|---|
| EP | 0995477 | 4/2000 |
| EP | 1005904 | 6/2000 |
| EP | 1064978 | 1/2001 |
| FR | 2773144 | 7/1999 |
| JP | 10165818 | 6/1998 |
| JP | 2006142160 | 6/2006 |
| WO | 9925461 | 5/1999 |
| WO | 0226355 | 4/2002 |

OTHER PUBLICATIONS

Search Report for FR 0753889, Oct. 2007.
PCT Written Opinion for PCT/FR2008/050424, Dec. 2009.

* cited by examiner

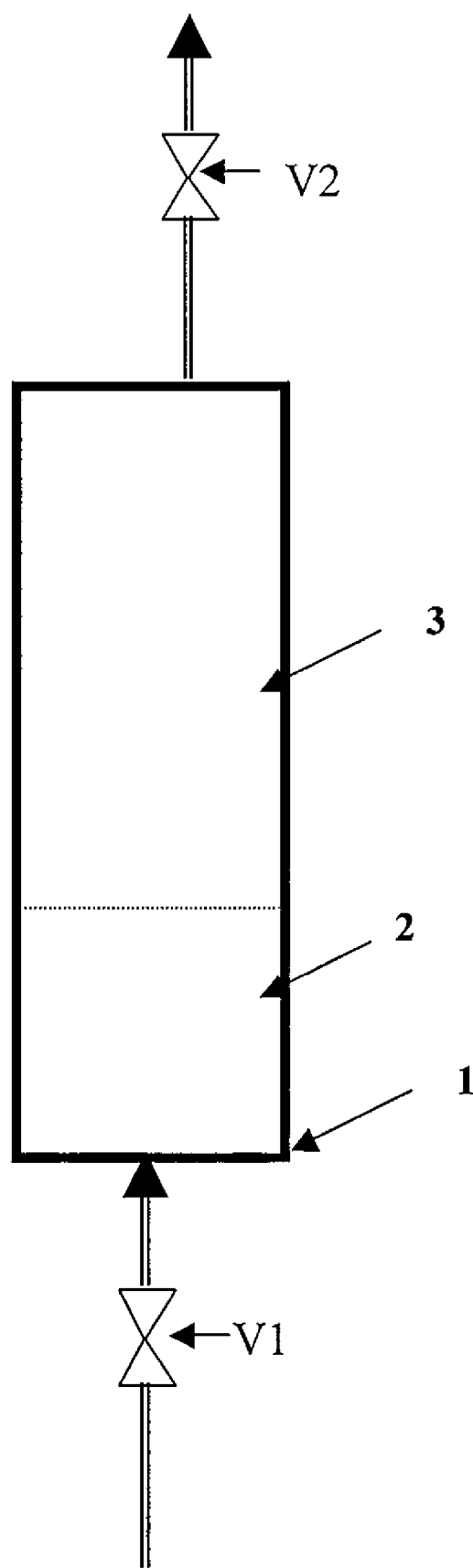

METHOD FOR REMOVING $N_2O$ FROM A GASEOUS FLOW

This application is a §371 of International PCT Application PCT/FR2008/050424, filed Mar. 13, 2008.

FIELD OF THE INVENTION

The invention relates to a method for purifying gas mixtures mainly containing nitrous oxide, nitrogen and oxygen, and possibly impurities, in particular water vapor and carbon dioxide, in particular a gas stream exhaled by a patient receiving a gas mixture of $N_2O$ and $O_2$.

BACKGROUND

Nitrous oxide ($N_2O$), also called laughing gas, has many applications.

It is used in particular in anesthesia and in analgesia for treating pain, for example in a mixture of about 50% by volume of $N_2O$ and 50% by volume of $O_2$.

In anesthesia and in analgesia, the $N_2O$-rich gas mixture is first inhaled by the patient, and a large part of the $N_2O$ is then found in the gases exhaled by the patient, mixed in particular with high proportions of $CO_2$ and water vapor.

Thus, for a mixture containing 50% by volume of $O_2$ and 50% by volume of $N_2O$ which is inhaled by a patient, the gases exhaled by this patient contain $N_2O$ saturated with moisture, about 4% by volume of $CO_2$, and over 40% by volume of oxygen.

It is in fact important to remove the $N_2O$ from the gases exhaled by the patient because it risks being present in the indoor air of the buildings and accumulating therein over time.

It is in fact vitally important to prevent such an accumulation of $N_2O$ in hospital buildings, because undesirable effects have been observed during the intense and frequent inhalation of $N_2O$, such as a vitamin B12 deficiency in the exposed persons.

$N_2O$ recovery and removal by catalysis has already been proposed, in particular by documents U.S. Pat. No. 4,259,303, WO-A-9925461, U.S. Pat. No. 2,006,008401, FR-A-2773144, JP-A-2006142160, EP-A-0698411 and JP-A-10165818.

However, this solution is complicated because it involves the use of transition metal compounds, some of which are costly and not easy to prepare. Moreover, the impurities present in the gas to be treated may poison and denature the catalyst. Besides, these methods require heating to several hundred ° C., with all the attendant complications and energy consumption.

Furthermore, document EP-A-0 995 477 proposes a method for adsorbing only small proportions of $N_2O$ present in atmospheric air, that is about a few ppm by volume. However, this document does not propose any solution for removing $N_2O$ when it is present in a volumetric proportion of several % or even several tens of %.

Accordingly, it has not hitherto been possible effectively to remove the nitrous oxide exhaled by the patient, which ends up staying in treatment rooms and similar areas of hospital buildings.

In view of this, there is a need for improved methods for treating feed gas streams containing nitrous oxide in a proportion of at least 5% by volume, preferably at least 10 to 20% by volume, in particular gas mixtures containing $N_2O$, oxygen, water vapor and a few % of $CO_2$, in order to increase the removal of $N_2O$ exhaled by the patients in hospital or similar buildings.

SUMMARY OF THE INVENTION

The present invention provides for a method for purifying a feed gas stream that contains at least 5% by volume of $N_2O$ and oxygen, in which a) at a temperature between 20° C. and 40° C. and at a pressure between 0.80 bar and 1.30 bar, the feed gas stream is placed in contact with a main adsorbent that comprises at least one zeolite exchanged to over 50% by one or more metal cations and has a $N_2O$ adsorption capacity higher than 80 $Ncm^3/g$, measured at 1 bar and 20° C., in order to adsorb at least part of the $N_2O$ from said stream and to produce a purified gas stream, and b) a purified gas stream is recovered, the purified gas stream having a $N_2O$ content lower than the $N_2O$ content of the feed gas stream placed in contact with the main adsorbent in step a).

DETAILED DESCRIPTION OF THE INVENTION

One solution claimed by the present invention is a method for purifying a feed gas stream that contains at least 5% by volume of $N_2O$ and oxygen.

In this process, at a temperature between 20° C. and 40° C. and at a pressure between 0.80 bar and 1.30 bar, the feed gas stream is placed in contact with a main adsorbent. The adsorbent comprises at least one zeolite exchanged to over 50% by one or more metal cations and having a $N_2O$ adsorption capacity higher than 80 $Ncm^3/g$, measured at 1 bar and 20° C., in order to adsorb at least part of the $N_2O$ from said stream and to produce a purified gas stream. A purified gas stream is recovered, having a $N_2O$ content lower than the $N_2O$ content of the feed gas stream placed in contact with the main adsorbent in step a).

Depending on the case, the inventive method may comprise one of the following features:
- the feed gas stream placed in contact with the main adsorbent in step a) contains at least 10% by volume of $N_2O$, preferably at least 20%, more preferably at least 30% and even more preferably at least 40% by volume of $N_2O$;
- in step (b) a purified gas stream is recovered containing less than 10% by volume of $N_2O$, preferably less than 5% by volume of $N_2O$, more preferably less than 3% by volume of $N_2O$;
- the feed gas stream placed in contact with the main adsorbent in step a) contains at least 30% by volume, preferably at least 40% by volume, of $N_2O$ and in step b), a purified gas stream is recovered containing less than 10% by volume of $N_2O$, preferably less than 5% by volume of $N_2O$;
- the feed gas stream placed in contact with the main adsorbent in step a) contains less than 80% by volume of $N_2O$, preferably less than 70% by volume of $N_2O$;
- the main adsorbent consists of particles having an average size of between 0.5 and 5 mm; this dimension corresponds either to a diameter if the particles are spherical, or to the greatest length if the particles are ellipsoidal in particular;
- the main adsorbent has an adsorption kinetics of between 2 and 20 $sec^{-1}$, preferably lower than 10 $sec^{-1}$; the kinetics is measured at 25° C. and 1 bar to absolute pressure. The breakthrough curve is measured from a mixture of $O_2$ containing less than 10% of $N_2O$. The kinetic constant is that of the LDF (linear driving force);

the feed gas stream, while passing through the main adsorbent in step a), undergoes a pressure drop of less than 20 mbar, preferably less than 5 mbar;

the zeolite is of type A, X, LSX, Mordenite, Offretite, Chabazite, Clinoptilolite or Erionite;

the zeolite is exchanged by one or more metal cations selected from $Na^+$, $Li^+$, $K^+$, $Ca^{2+}$, $Mg^{2+}$ and $Ba^{2+}$, and combined or not with transition metals, preferably selected from silver, zinc or copper;

the main adsorbent has an $N_2O$ adsorption capacity at 1 bar and 20° C. that is higher than 90 $Ncm^3/g$;

the feed gas stream also contains water vapor, $CO_2$ and/or argon and/or nitrogen and is preferably exhaled by a patient;

the $CO_2$ adsorption capacity of the main adsorbent, measured at 0.04 bar and 20° C., is higher than or equal to 30 $Ncm^3/g$, preferably higher than 50 $Ncm^3/g$;

the method further comprises, prior to step a), placing the feed gas stream in contact with a secondary adsorbent comprising a desiccant capable of trapping all or part of the water vapor contained in the gas stream, preferably alumina;

the method further comprises the step of regenerating the adsorbent under vacuum, that is at a pressure between 10 and 300 mbar, by flushing a dry and inert gas, heated to a temperature between 80 and 250° C., preferably to between 125 and 200° C.;

the flow rate of the feed gas stream to be purified is between 1 and 30 Nliters/min, preferably between 8 and 15 Nliters/min;

the feed gas stream is a gas stream exhaled by a human being or an animal.

In view of a filing in the USA, an inhalatory anesthesia method claim of the following type must be added to the description.

The invention also relates to a method for inhalatory anesthesia of a human being or an animal, in which:

i) an anesthetic gas mixture containing oxygen and a proportion of $N_2O$ higher than 30% by volume is administered by inhalation to a human being or to an animal;

ii) at least part of the gases exhaled by said human or animal is recovered;

iii) all or part of the gases exhaled and recovered in step ii) are subjected to a purification method according to the invention.

Depending on the case, the anesthesia method of the invention may comprise one or more of the following features:

the human being is a patient, the anesthetic gas mixture only contains oxygen and $N_2O$, the anesthetic gas mixture is formed of 50% $N_2O$ and 50% $O_2$ by volume, the anesthetic gas mixture contains a sufficient proportion of $N_2O$ to cause or maintain anesthesia in said human or animal;

the anesthetic gas mixture is administered to the airways of said human or animal, for example by means of a mask or similar, preferably connected to an anesthesia ventilator or to any appropriate gas administration apparatus designed to supply the patient with anesthetic gas.

The invention is described below in greater detail with reference to FIG. 1 provided for illustration.

The gas to be purified is a gas mixture having the composition of the gases exhaled by a patient undergoing an inhalatory anesthesia by means of a gas mixture formed of 50% $N_2O$ and 50% $O_2$ (% by volume) approximately.

The gas mixture containing $N_2O$, $CO_2$, water vapor and oxygen, and even argon and/or nitrogen, is recovered and sent via the valve V1 to the adsorber 1 consisting of an upstream bed of alumina 2, in which the water is retained, followed by a downstream bed of zeolite, for example a zeolite 13 X, in which the $N_2O$ and $CO_2$ are retained by adsorption. The purified gas consisting mainly of oxygen is collected, at the adsorber outlet, via the valve V2, and is then either recycled or discharged to the atmosphere.

By way of example, a respirator or a humidifier coupled to an artificial lung were used to simulate a patient. The gas to be purified had the following composition: 4.25% $CO_2$, 46.25% $O_2$ and 49.5% $N_2O$.

The gas was sent to the respirator with the following settings: 10 l/min, 15 minutes per cycle. The gas leaving the respirator was sent to the humidifier, then into the artificial lung, set to the characteristics of an adult patient (volume 600 ml, resistance 5 mbar/(l/s), compliance 23 ml/mbar). The outlet of the artificial lung was connected to the adsorber. The adsorber was filled with 15 kg of zeolite type ZEOCHEM Z10-02 ND, bead size 1.6-2.6 mm. The zeolite was activated overnight at about 325° C. under dry nitrogen stream, with a flow rate to renew the volume about 10 times per hour. It contained 100% of $Na^+$ cations. The temperature of the room was between 17° C. and 20° C. The gas leaving the adsorber was quantitatively analyzed by Fourier transform infrared analysis (FT-IR).

The operation consisted in simulating medical "procedures" lasting 15 minutes, with a 15 minute intermission between each.

Two tests were performed, respectively with a cylindrical adsorber and a "horseshoe" adsorber, corresponding to the commercial system. No significant difference was observed between the two geometries. During the first 12 procedures, no trace of $N_2O$ was detected at the outlet, and in the 13$^{th}$ procedure, the $N_2O$ breakthrough was observed. The flow rate was then maintained as such, and it took 25 minutes to recover the inlet composition at the outlet.

It appears that, related to the quantity of zeolite, the two adsorber geometries yield comparable results, corresponding to a practical adsorption capacity of about 60 Nl/kg. The pure substance adsorption isotherm of the zeolite used is 110 Nl/kg at 20° C. and 1 bar. The difference between practical and pure substance capacity stems from the coadsorption with water and $CO_2$ and also the length of the adsorption front, which requires stopping as soon as the first traces are found at the outlet.

The pure substance adsorption capacity of the zeolite must be between 80 $Ncm^3/g$ and 120 $Ncm^3/g$ at 1 bar and 20° C., because it is for these values that the quantity of adsorbent is adapted to the shape and volume of the cylinder. In fact, the cylinder used is capable of containing 1500 Nl of mixture, corresponding to ten procedures: in the capacity range claimed, no more than 20 kg of adsorbent must be used, due to the weight, and it is not advantageous to use less than 12 kg of adsorbent, because the volume of adsorbent must remain comparable to that of the cylinder and its equipment.

The various beds of "polluted" adsorbents can then be stored in the closed adsorber at the end of the operation, while awaiting regeneration. The "polluted" beds are then regenerated in countercurrent flow, using a regeneration gas heated to a temperature between 80 and 250° C., preferably between 125° C. and 200° C. The nitrous oxide, carbon dioxide and water vapor are thus desorbed from the various adsorbent beds and recovered.

The nitrous oxide is then removed by venting to the outdoor air of the building, destroyed or re-used after purification and sterilization.

The nitrous oxide desorbed during the regeneration phase is in concentrated form, because it accounts for 50% to 90% by volume of the gas stream issuing from the desorption of the adsorbents.

A residence time of about 1 hour of the adsorbents at the regeneration temperature is sufficient to desorb said adsorbents.

Preferably, the regeneration is carried out in the adsorber itself, but a regeneration outside the adsorber is feasible, by direct handling of the adsorbents. The regeneration gas is preferably dry, that is it contains no more than 10 ppm of water vapor, preferably no more than 1 ppm. It is unreactive to the adsorbents. It may be air, oxygen, nitrogen or an oxygen-nitrogen mixture having a variable composition.

Alternatively, the regeneration can be carried out by placing the adsorber under dynamic vacuum, at a pressure lower than 0.01 mbar, preferably lower than 0.01 mbar, the other conditions remaining unchanged.

After regeneration, the adsorbent is allowed to cool inside or outside the adsorber, and then stored in the closed adsorber.

In general, the pressure of the gas stream exhaled by the patient, that is of the exhaled gases, is generally between 970 mbar and 1080 mbar absolute. These gases exhaled by the patient are recovered for example by means of a mask or similar, and then treated directly by contacting the adsorbent or adsorbents as explained above, or optionally after filtration and/or compression to a pressure lower than 1.5 bar absolute.

The temperature of the feed gas stream entering the adsorption column is in the 5 to 45° C. range, preferably between 15 and 40° C. Accordingly, the operating temperature of the adsorber 1 during steps (a) and (b) of the inventive method is also between 5 and 45° C., preferably between 15° C. and 40° C., and even more preferably between 25° C. and 35° C.

It is preferable to maximize the adsorption of $CO_2$, although this competes with the $N_2O$. This is because $CO_2$ is adsorbed more strongly than $N_2O$ and prevents the latter's adsorption. It is therefore important to minimize the zone of $CO_2$-saturated adsorbent, which is equivalent to maximizing the quantity of $CO_2$ stored related to the mass of adsorbent.

A single adsorbent bed containing zeolite can be used in the context of the invention. However, since the water vapor can be removed by the zeolite itself, it hinders the adsorption of $CO_2$ and in particular that of $N_2O$.

Accordingly, a bed of alumina, placed upstream of the bed containing zeolite, serves to at least partially dry the feed gas stream, that is to remove at least part of the water vapor that it conveys. Although alumina is preferred, other desiccant materials, that is materials capable of trapping water vapor, such as silica gel or zeolites, can be used.

The flow to be treated may be intermittent, flowing for example for no more than 60% of the time. In fact, the gas stream exhaled by the patient has a variable flow rate due to respiration.

The main adsorbent according to the invention may comprise grains or particles of adsorbent of which the actual solid adsorbent phase is "aerated" by a volume dispersed porosity which ensures transport of the gases.

In fact, the porosity can be defined by the expression: $q = \epsilon \ast C_p + (1-\epsilon) \ast C_s$, where $\epsilon$ is the porosity of the adsorbent grain, q the total concentration in the adsorbent grains in mole/m$^3$, $C_p$ the concentration in mole/m$^3$ in the gas phase of the porosity and $C_s$ the concentration in the solid adsorbent phase in mole/m$^3$.

Furthermore, we have $$\frac{dq}{dt} = a_k \times (\overline{C}_p - C_p),$$

where $a_k$ represents the adsorption kinetics and $\overline{C}_p$, the gas concentration that would correspond to equilibrium with the adsorbent grains.

Accordingly, a volume dispersed porosity which ensures transport of the gases corresponds to an adsorption kinetics of the main adsorbent of between 2 and 20 sec$^{-1}$, preferably lower than 10 sec$^{-1}$. This is contrary to the prior art, which aims for maximum adsorption kinetics. It is normally attempted to have the shortest possible adsorption front, in order to delay the exit of the adsorbed impurity.

Furthermore, the high proportion of $N_2O$ (above 30% or even 40%) spontaneously shortens the adsorption front by a "shock front" effect resulting from the curvature of the isotherm. In fact, when the adsorption isotherm is convex, the adsorption front tends to be as vertical as possible, because the high concentration portions advance faster than the low concentration portions and therefore catch up with the latter.

The adsorption kinetics is important because it determines the length of the adsorption front in the adsorbent and, in consequence, the rate of use of the adsorbent. In the context of the present invention, rate of use means the ratio of the actual adsorption capacity to the theoretical adsorption capacity.

Accordingly, the rate of use according to the invention must be preferably equal to about ⅔ for $N_2O$, ¼ for $CO_2$ and ⅛ for water vapor.

Furthermore, in exchange for a lower requirement on the kinetics, a lower pressure drop is obtained, because larger particles and/or a denser adsorbent can be used.

Thus, the pressure drop must always be lower than 20 mbar, preferably lower than 5 mbar, and the adsorbent particle size, which determines both the adsorption kinetics and the pressure drop, must be between 0.5 mm and 5 mm equivalent diameter in order to obtain a good compromise between these two factors. The particles tend to be in the form of beads, extruded or crushed material, preferably beads.

It should be noted that the adsorber configuration may be cylindrical, with a radial or axial flow, or it may have a compact geometry, optionally with internal elements (baffles) designed to facilitate the contact between the gas and the adsorbent.

What is claimed is:

1. A method for purifying exhaled anesthesia gas containing oxygen and at least 20% by volume of $N_2O$, wherein:
   (a) at a temperature between 20° C. and 40° C. and at a pressure between 0.80 bar and 1.30 bar, the exhaled anesthesia is placed in contact with a main adsorbent, comprising at least one zeolite exchanged to over 50% by one or more metal cations, wherein the main adsorbent has an adsorption kinetics of less than 10 sec$^{-1}$, and having a $N_2O$ adsorption capacity higher than 80 Ncm$^3$/g, measured at 1 bar and 20° C., in order to adsorb at least part of the $N_2O$ from the stream and to produce a purified gas stream, and
   (b) a purified gas stream is recovered, having a $N_2O$ content lower than the $N_2O$ content of the exhaled anesthesia gas placed in contact with the main adsorbent in step a).

2. The method of claim 1, wherein in step b), a purified gas stream is recovered containing less than 10% by volume of $N_2O$.

3. The method of claim 1, wherein the exhaled anesthesia qas placed in contact with the main adsorbent in step a) contains at least 30% by volume of $N_2O$ and in that in step b) a purified gas stream is recovered containing less than 10% by volume of $N_2O$.

4. The method of claim 1, wherein the exhaled anesthesia qas placed in contact with the main adsorbent in step a) contains less than 80% by volume of $N_2O$.

5. The method of claim 1, wherein the zeolite is of type A, X, LSX, Mordenite, Offretite, Chabazite, Clinoptilolite or Erionite.

6. The method of claim 1, wherein the zeolite is exchanged by one or more metal cations selected from $Na^+$, $Li^+$, $K^+$, $Ca^{2+}$, $Mg^{2+}$ and $Ba^{2+}$.

7. The method of claim 6 wherein the zeolite is also combined with one or more transition metals.

8. The method of claim 7, wherein the transition metals are selected from silver, zinc and copper.

9. The method of claim 1, wherein the main adsorbent has an $N_2O$ adsorption capacity at 1 bar and 20° C. that is higher than 90 $Ncm^3/g$.

10. The method of claim 1, wherein the exhaled anesthesia gas also contains water vapor, $CO_2$ and/or argon and/or nitrogen.

11. The method of claim 1, wherein the $CO_2$ adsorption capacity of the main adsorbent, measured at 0.04 bar and 20° C., is higher than or equal to 30 $Ncm^3/g$.

12. The method of claim 1, wherein the method further comprises, prior to step a), placing the exhaled anesthesia gas in contact with a secondary adsorbent comprising alumina in order to remove at least part of the $H_2O$ and/or the $CO_2$.

13. The method of claim 1, wherein the flow rate of the exhaled anesthesia qas to be purified is between 1 and 30 Nliters/min.

14. The method of claim 1, wherein the exhaled anesthesia gas was exhaled by a human being.

15. The method of claim 1, wherein in step b), a purified gas stream is recovered containing less than 5% by volume of $N_2O$.

16. The method of claim 1, wherein:
the exhaled anesthesia gas placed in contact with the main adsorbent in step a) contains from at least 30% by volume to less than 70% by volume of $N_2O$, an $N_2O$ adsorption capacity, measured at 1 bar and 20° C., that is between 90 and 120 $Ncm^3/g$ and a $CO_2$ adsorption capacity, measured at 0.04 bar and 20° C., higher than or equal to 50 $Ncm^3/g$;
the zeolite is of type A, X, LSX, Mordenite, Offretite, Chabazite, Clinoptilolite or Erionite and is exchanged by one or more metal cations selected from $Na^+$, $Li^+$, $K^+$, $Ca^{2+}$, $Mg^{2+}$ and $Ba^{2+}$;
in step b) the purified gas stream is recovered containing less than 5% by volume of $N_2O$; and
the flow rate of the exhaled anesthesia qas to be purified is between 8 and 15 Nliters/min.

17. The method of claim 16 wherein the zeolite is also combined with one or more transition metals.

* * * * *

UNITED STATES PATENT AND TRADEMARK OFFICE
CERTIFICATE OF CORRECTION

PATENT NO.          : 8,246,721 B2
APPLICATION NO.     : 12/530715
DATED               : August 21, 2012
INVENTOR(S)         : Serge Moreau It is certified that error appears in the above-identified patent and that said Letters Patent is hereby corrected as shown below:

In Column 7, line 2, replace the word "qas" with the word --gas--.

In Column 7, line 7, replace the word "qas" with the word --gas--.

In Column 8, line 4, replace the word "qas" with the word --gas--.

In Column 8, line 27, replace the word "qas" with the word --gas--.

Signed and Sealed this
Twentieth Day of November, 2012

David J. Kappos
*Director of the United States Patent and Trademark Office*